(12) United States Patent
Guyton et al.

(10) Patent No.: US 10,314,482 B2
(45) Date of Patent: Jun. 11, 2019

(54) EYE ALIGNMENT MONITOR AND METHOD

(71) Applicant: THE JOHNS HOPKINS UNIVERSITY, Baltimore, MD (US)

(72) Inventors: David L. Guyton, Baltimore, MD (US); Kristina Irsch, Baltimore, MD (US); Howard S. Ying, Baltimore, MD (US); Boris I. Gramatikov, Baltimore, MD (US); Robert Geary, Baltimore, MD (US); Jing Tian, Parkville, MD (US); Kurt Simons, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 41 days.

(21) Appl. No.: 15/121,814

(22) PCT Filed: Feb. 27, 2015

(86) PCT No.: PCT/US2015/017920
§ 371 (c)(1),
(2) Date: Aug. 26, 2016

(87) PCT Pub. No.: WO2015/131009
PCT Pub. Date: Sep. 3, 2015

(65) Prior Publication Data
US 2017/0014026 A1    Jan. 19, 2017

Related U.S. Application Data (60) Provisional application No. 61/946,145, filed on Feb. 28, 2014.

(51) Int. Cl.
*A61B 3/113*    (2006.01)
*A61B 3/00*    (2006.01)
(Continued)

(52) U.S. Cl.
CPC ............ *A61B 3/113* (2013.01); *A61B 3/0025* (2013.01); *A61B 3/0091* (2013.01); *A61B 3/14* (2013.01); *G02B 26/0833* (2013.01); *A61B 3/085* (2013.01)

(58) Field of Classification Search
CPC ......... A61B 3/113; A61B 3/14; A61B 3/0091; G02B 26/0833
See application file for complete search history.

(56) References Cited

U.S. PATENT DOCUMENTS

5,502,514 A    3/1996    Vogeley et al.
6,152,563 A    11/2000    Hutchinson et al.
(Continued)

*Primary Examiner* — Jack Dinh
(74) *Attorney, Agent, or Firm* — Johns Hopkins Technology Ventures (57) ABSTRACT

An eye alignment monitor and method are described for the detection of variability of the relative alignment of the two eyes with each other, thereby detecting deficits of binocular function, for use as a screening device for these abnormalities especially in infants and young children. Each embodiment includes means for tracking of the positions of a subject's two eyes simultaneously, and furthermore includes repetitive calculation of the relative positions of the two eyes with respect to each other. The embodiments do not require fixation by either eye on a specific point. Typically, a movie on a video display is used for viewing by the subject. Variability of relative alignment of the two eyes with each other is typically determined by variability of the relative positions of images of the pupils of the eyes with respect to each other over time.

20 Claims, 5 Drawing Sheets

(51) Int. Cl.
  *G02B 26/08* (2006.01)
  *A61B 3/14* (2006.01)
  *A61B 3/08* (2006.01)

(56) References Cited

U.S. PATENT DOCUMENTS

| | | |
|---|---|---|
| 7,110,582 B1 | 9/2006 | Hay |
| 2004/0005083 A1 | 1/2004 | Fujimura et al. |
| 2009/0103048 A1 | 4/2009 | Tsukiji |

EYE ALIGNMENT MONITOR AND METHOD

CROSS-REFERENCE TO RELATED APPLICATIONS

This application is a 35 U.S.C. § 371 U.S. national entry of International Application PCT/US2015/017920, having an international filing date of Feb. 27, 2015, which claims the benefit of U.S. Provisional Application No. 61/946,145, filed Feb. 28, 2014, the content of each of the aforementioned applications is herein incorporated by reference in their entirety.

FIELD OF INVENTION

The field of the currently claimed embodiments of this invention relates to eye alignment monitors, and more particularly to eye alignment monitors that assess the stability of the alignment of the two eyes with each other during viewing.

BACKGROUND

Current devices that monitor the relative alignment of the two eyes with each other use eye-tracking methods to determine the accuracy of fixation of each eye separately on a specified fixation point. The relative stability of the alignment of the two eyes with each other is thereby inferred by comparison of the accuracy of fixation of the two eyes separately.

Numerous eye-tracking devices and methods are known to the art. Specifically useful, especially with children, are those methods that determine the gaze point of an eye from a distance, without requiring apparatus worn on the head of the subject. Many such methods infer the direction of gaze from the position of the pupil in a video image as the eye looks in one direction or the other. Such pupil-tracking methods require the head to be still and require the obtaining of multiple calibration points within the visual scene, involving the recording of pupil positions versus respective test points in the visual scene, for accurate estimation of the gaze point of the eye during subsequent eye tracking and recording.

Other eye-tracking devices and methods use not only the position of the pupil in a video image, but also use the position of the corneal light reflection of a small source of light. The image of the corneal light reflection is a virtual image approximately 1 mm posterior to the pupil in the human eye, so that both the pupil and the corneal light reflection can be imaged sharply by the recording camera. When the eye moves in one direction, both the pupil and the corneal light reflection move in that same direction but at different speeds, with the corneal light reflection moving only about half as fast as the movement of the pupil. Therefore the position of the corneal light reflection, with respect to the position of the pupil, with appropriate calibration, yields an estimate of the gaze point, in relation to the positions of the camera and the small source of light, which is reasonably independent of head position. If the small source of light is placed conjugate to the aperture of the camera via a beam splitter, the video image of the eye has a bright pupil, because the eye's optics return the reflected light from the retina back towards the source, where it enters the camera aperture, yielding the bright pupil in the image. If the small source of light is placed eccentric enough to the camera aperture, the pupil remains dark, although the corneal light reflection of the source of light is still present, somewhat eccentric. Both bright-pupil and dark-pupil methods have been used successfully for eye tracking.

The primary remaining disadvantage of eye tracking devices and methods that use images of the pupil, and/or images of lights reflected by the cornea, to estimate the gaze point, is the necessity to calibrate the device for each individual eye, given the variability of eye size, corneal curvature, and pupil positions in the population.

Other devices and methods exist for detecting when an eye is looking in a given direction. The fovea is that part of the retina where vision is most acute, and this is the part of the retina that is aimed at the object of regard during fixation. The nerve fibers in the retina radiate out from the fovea like the spokes of a bicycle wheel. These nerve fibers have a small amount of "form" birefringence that changes the nature of polarized light that passes through them, with the type and amount of polarization change varying with the angular direction of the nerve fibers. Polarized incident light that is reflected from the back of the eye passes through these nerve fibers twice, and the resulting change in the polarization of the double-pass light can be detected by sensors near the source of the polarized light. By scanning a spot of light about in a specified manner on the retina, a spatial birefringence-produced polarization signature can be obtained of that patch of nerve fibers encountered by the scan. Specifically, if a circular scan of the spot of light is centered exactly on the fovea, polarization changes can be detected in the double-pass light that occur at exactly twice the frequency of the scan, as described in U.S. Pat. No. 6,027,216. A high level of this double-frequency signal thus detects eye fixation on a spot in the center of the circular scan of light. This method of detecting eye fixation in a given direction has been termed "retinal birefringence scanning."

Detection of eye fixation via retinal birefringence scanning does not require calibration in specific directions of gaze as do the video-based pupil-tracking methods, because retinal birefringence scanning detects the anatomic fovea directly by sensing centration of the circular scan on the radial nerve fibers emanating from the fovea. But using retinal birefringence scanning for eye tracking, rather than simply for eye fixation detection, becomes complicated because the polarization signatures of many areas of the nerve fibers away from the fovea are neither unique nor of high amplitude.

There are still other methods for tracking the positions of the eyes. These include tracking the positions of only the corneal light reflections from the eyes, tracking the positions of the corneal/scleral junctions of the eyes, tracking the positions of anatomic features of the eyes using optical coherence tomography, and tracking the positions of the eyes using scleral search coil recordings.

Recently it has been discovered that eyes with amblyopia (decreased vision in an eye caused by misalignment or defocus in early life), typically have a small amount of misalignment with the other eye when viewing a small fixation target. U.S. Pat. No. 7,959,292 B2 describes a binocular retinal birefringence scanning device which, by detecting such small amounts of misalignment on a fixation target, can identify children (or adults) with amblyopia. Even more recently it has been discovered that eyes with amblyopia do not fixate steadily on a small target, either under monocular or binocular conditions. [See González E G, et al. *Invest Ophthalmol Vis Sci.* 2012; 53(9):5386-94, and Subramanian V, Jost R M, Birch E E. *Invest Ophthalmol Vis Sci.* 2013; 54(3):1998-2003.] It therefore appears that there is not a constant misalignment of the amblyopic eye, but rather a varying misalignment.

The eyes normally move tightly together in various directions of gaze, with this "conjugacy" of the movements of the two eyes regulated and maintained by the normal binocular vision system. When the eyes have roughly equal vision and are working perfectly well together ("fusing" peripherally and centrally), the brain continually senses if and when the eyes begin to become misaligned, via impending double vision, and makes fine adjustments to the signals to the eye muscles to keep the eyes aligned. Over time, with repetition of these signals occurring in various directions of gaze, "vergence adaptation" causes a "map" to be established in the brain, a map of how much each of the 12 eye muscles should be stimulated to maintain alignment of the two eyes with each other in each direction of gaze and at each distance from the individual. The result is that the eyes move tightly together when binocular vision is normal, both remaining fixated tightly on the object of regard. Even when one eye is covered, its movement behind the cover is quite conjugate with the movement of the fixing eye—again, when binocular vision is normal.

This normal conjugacy of the movements of the two eyes with one another has been documented for decades by binocular eye tracking when subjects are instructed to look quickly from one specific point to another (such a quick eye movement is called a "saccade"). To be sure, horizontal binocular saccades have been shown to be disconjugate when one eye is amblyopic [Maxwell G F, Lemij H G, Collewijn. Conjugacy of saccades in deep amblyopia. *Invest Ophthalmol Vis Sci.* 1995; 36:2514-2522], and also horizontally disconjugate when strabismus is present (misalignment of the two eyes) [Kapoula Z, Bucci M P, Eggert T, Garraud L. Impairment of the binocular coordination of saccades in strabismus. *Vision Res.* 1997; 37:2757-2766]. Furthermore, in the presence of strabismus, saccades have been shown to be disconjugate in direction as well as in amplitude [Walton W W G, Ono S, Mustari M. Vertical and oblique saccade disconjugacy in strabismus. *Invest Ophthalmol Vis Sci.* 2014; 55:275-290].

Thus deficits of binocular function (strabismus, amblyopia, monocular blindness, etc.) cause disconjugacy of eye movements and disconjugacy of the moment-to-moment positions of the two eyes with respect to one another. Indeed, we have experimentally confirmed that, in the presence of deficits of binocular function (occurring with strabismus, amblyopia, monocular blindness, traumatic brain injury, inebriation, fatigue, etc.), the positions of the two eyes vary with respect to one another during ordinary viewing. In the reverse, detecting variability of the alignment of the two eyes with each other (detecting "disconjugate" alignment over time) can serve as a means to screen for deficits of binocular function. The eye-tracking or fixation-detecting methods described above may be used for such a purpose, but each such method is subject to significant limitations, especially with infants and young children. For example, the pupil-tracking methods and corneal light reflex/pupil-tracking methods all require gaze calibration for proper functioning, with such calibration difficult if not impossible with infants and young children. The binocular retinal birefringence scanning method only detects the presence or absence of fixation of each eye separately; it does not easily detect the amount of misalignment.

Again, to date, devices that monitor the relative alignment of the two eyes with each other use eye-tracking methods to determine the accuracy of fixation of each eye separately on a specified fixation point. The relative stability of the alignment of the two eyes with each other has thereby been inferred by comparison of the accuracy of fixation of the two eyes separately. In one instance the relative horizontal positions of one eye with respect to the other have been calculated from binocular recordings during a fixation task [Raveendran R N, Babu R J, Hess R F, Bobier W R. Transient improvements in fixational stability in strabismic amblyopes following bifoveal fixation and reduced interocular suppression. *Ophthalmic Physiol Opt* 2014. doi: 10.1111/opo.12119]. In this case, however, this "relative position" technique was to determine how long a bifoveal fixation condition persisted after an initial 10 seconds of bifoveal fixation. The technique used a specific fixation target and was not used for a measurement of the overall variability of the conjugacy of the two eye's positions over time. Likewise, it was not used for the identification of deficits of binocular function.

Note that all of the methods discussed above have required the subject to gaze at, or follow, a small fixation target, a task that is not reliably performed by infants or small children, who comprise the primary population that needs to be screened for deficits of binocular function. Detecting these deficits early in life enables more timely and more effective therapy for lifelong improvement. A method and device are therefore needed to detect variability in the moment-to-moment alignment of the two eyes with each other, to thereby detect deficits of binocular function, without requiring specified gaze on small fixation targets.

SUMMARY

The foregoing needs are met, to a great extent, by the present invention wherein in one aspect, an eye alignment monitor and method, for the detection of variability of the relative alignment of the two eyes with each other, includes means for tracking of the positions of two eyes simultaneously, and furthermore includes repetitive calculation of the position of one eye with respect to the other by subtraction of the position of one pupil image with respect to the position of the other pupil image, without requiring fixation of either eye on a specific point. Variability of alignment is thus determined by variability of the differences in the positions of the two pupil images over time, for the purpose of screening for deficits of binocular function. Typically, an attention-attracting visible object such as a movie on a video display is used for viewing by the subject, although a variety of stimuli may be suitable to attract the subject's gaze—for example a specified fixation point which is stationary or moving, an extended scene containing a specified fixation point which is stationary or moving, or an extended scene not containing a specified fixation point. A visible object seen by only one eye will suffice. In the extreme, even a sound in total darkness toward which the subject "looks" can be suitable.

In accordance with an aspect of the present invention, an eye alignment monitor and method, for the detection of variability of the relative alignment of the two eyes with each other, includes imaging the pupils of the two eyes onto the surface of a digital image sensor, for example a charge-coupled device (CCD) or a complementary metal-oxide-semiconductor (CMOS) device, using image processing to locate the positions of each pupil image, and calculating the variability of the relative position of one pupil image with respect to the other over time as a measure of the variability of the relative alignment of the two eyes with each other.

In accordance with another aspect of the present invention, an eye alignment monitor and method, for the detection of variability of the relative alignment of the two eyes with each other, includes the use of two analog X-Y position sensors, imaging the pupil of each eye onto the surface of its respective X-Y position sensor to determine the centroid of that pupil's image, and calculating the variability of the relative positions of the centroids of the two pupil images with respect to each other over time as a measure of the relative variability of the alignment of the two eyes with each other.

In accordance with another aspect of the present invention, an eye alignment monitor and method, for the detection of variability of the relative alignment of the two eyes with each other, includes the use of one analog X-Y position sensor, imaging the pupil of each eye in turn in an alternating manner onto the surface of the analog X-Y position sensor via reflection from a digital micro-mirror device (DMD), determining the centroid of each pupil's image from the momentary time that it falls on the surface of the analog X-Y position sensor, and calculating the variability of the relative positions of the centroids of the two pupil images with respect to each other over time as a measure of the relative variability of the alignment of the two eyes with each other.

In accordance with another aspect of the present invention, an eye alignment monitor and method, for the detection of variability of the relative alignment of the two eyes with each other, includes a near-infrared light-emitting diode (IRED) as the light source, with an aperture placed conjugate to the IRED to capture the light retro-reflected from the retina of each eye and imaged back toward the light source by the eye.

In accordance with another aspect of the present invention, an eye alignment monitor and method, for the detection of variability of the relative alignment of the two eyes with each other, includes a point light source (such as a "point source" LED [an LED which uses a tiny aperture anterior to the light emitting chip, such as available from Marktech Optoelectronics], a semi-luminescent diode, a laser diode, or a gas or solid-state laser with a diverging lens) placed optically conjugate to, and thus appearing to coincide with, the visible object being viewed. An aperture is placed conjugate to the point light source to capture the light retro-reflected from the retina and imaged back toward the point light source by the eye, whereby the quality of the double-pass focus of the light from each eye in the plane of that aperture will indicate the goodness of focus of that eye on the desired object being viewed. The goodness of focus of the two eyes may be detected by imaging that conjugate aperture onto the surface of a CCD or CMOS image sensor and using image processing to analyze the double-pass blur images. Or the goodness of focus may be determined by imaging the light in the plane of that conjugate aperture from each of the two eyes onto the surface of one of two respective bull's-eye photodetectors, whereby defocus is detected by comparing the signal from the out-of-focus light striking the annulus component of the detector with the signal from the light striking the center component of the detector. If the signal from the center component of the detector is high relative to the signal from the annulus component, then the double-pass light is well-focused on the center component.

In accordance with another aspect of the present invention, an eye alignment monitor and method, for the detection of variability of the relative alignment of the two eyes with each other, includes a visible object, such as a movie on a video display, that is imaged at a far distance or at infinity for viewing by the subject, for the purpose of avoiding convergence of the eyes by the subject onto a near object, not only to avoid the undesirable effect of convergence in damping small eye movements, but also to avoid varying convergence which can interfere with the determination of variability of the relative alignment of the two eyes with each other.

In accordance with another aspect of the present invention, an eye alignment monitor and method, for the detection of variability of the relative alignment of the two eyes with each other, uses a visible object such as movie on a video display that is physically placed at a distance, for viewing by the subject, not only for the purpose of avoiding convergence of the eyes by the subject for the advantages just mentioned above, but also for the purpose of simplifying the construction and complexity of the detection device itself, without having to have the visible object incorporated within it.

In accordance with another aspect of the present invention, an eye alignment monitor and method, for the detection of variability of the relative alignment of the two eyes with each other, includes a visible object imaged or placed at a far distance for viewing by the subject, and also includes imaging the light source as if coming from the same far distance, taking into account the difference in chromatic aberration between the near infrared light of the light source and the visible light from the object being viewed, enabling judgment of the quality of the double-pass blur of the light source from each eye in order to assess the state of focus or defocus of the eyes.

BRIEF DESCRIPTION OF THE DRAWINGS

Further objectives and advantages will become apparent from a consideration of the description, drawings, and examples.

DETAILED DESCRIPTION

The presently disclosed subject matter will now be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides an eye alignment monitor and method for the detection of variability of the relative alignment of the two eyes with each other, thereby detecting deficits of binocular function, for use as a screening device for these abnormalities especially in infants and young children. Each embodiment includes means for tracking of the positions of a subject's two eyes simultaneously, and furthermore includes repetitive calculation of the relative positions of the two eyes with respect to each other. The embodiments do not require fixation by either eye on a specific point. Typically, a movie on a video display is used for viewing by the subject. Variability of relative alignment of the two eyes with each other is typically determined by variability of the relative positions of images of the pupils of the eyes with respect to each other over time.

Figure 1:
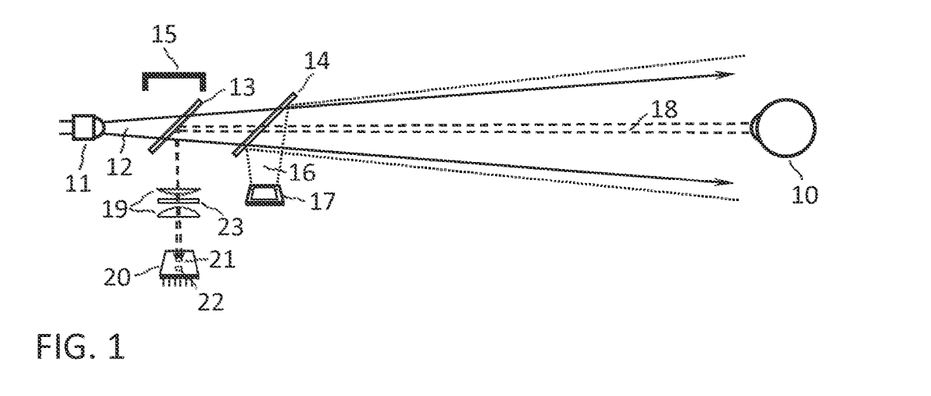
FIG. 1 illustrates a schematic diagram of an eye alignment monitor, using an IRED light source and a digital image sensor, according to an embodiment of the current invention.

FIG. 1 illustrates a schematic diagram of an eye alignment monitor for tracking the images of the pupils of both eyes of a subject simultaneously. Only the left eye 10 of the subject is shown, for ease of illustration. The right eye is on the far side of, and thus hidden by, illustrated left eye 10. A near-infrared light-emitting diode (IRED) 11 emits beam of light 12 that passes through beam splitters 13 and 14 to illuminate left eye 10 of the subject as well as the right eye on the far side of left eye 10. Beam splitter 13 is preferably a 50:50 beam splitter. Light trap 15 is provided to absorb the superiorly reflected light from beam splitter 13, preventing that light from returning back through beam splitter 13 to the detection system below. Beam splitter 14 is typically a dichroic beam splitter, transmitting the near-infrared light beam 12, and reflecting visible light beam 16 from video display 17. The movie shown on video display 17 is seen by both eyes of the subject via beam splitter 14 and is provided to attract the attention and the focus of the subject.

In FIG. 1, IRED 11 is positioned farther away from the subject's eyes than video display 17. This is because the chromatic aberration of the human eye causes near-infrared light to be focused deeper into the eye than visible light. The difference in refraction of the human eye between near-infrared light and visible light is approximately 0.75 to 1.00 diopter. By placing IRED 11 farther from the eyes than video display 17, the light beams 12 and 16 from the two sources become focused on the retinas of both eyes when the eyes are focused on the movie on video display 17. Although this arrangement maximizes the near-infrared light reflected back out of the eyes toward the source, when the eyes are focused on video display 17, such maximizing is not necessary for proper functioning of this particular embodiment of the invention. This arrangement will be necessary, however, in further embodiments described below.

Continuing in FIG. 1, that portion of near-infrared light beam 12 that enters the pupil of eye 10 is partially reflected by the rear inside surfaces (fundus) of the eye, and a portion of this reflected light [about 1/1000 of the original light beam entering the eye—see Miller J M, Hall H L, Greivenkamp J E, and Guyton D L. Quantification of the Bruckner test for strabismus. *Invest Ophthalmol Vis Sci.* 1995; 36:897-905] emerges from the pupil of eye 10, constituting reflected light beam 18, traveling back toward IRED 11, the original source. Reflected light beam 18 passes through beam splitter 14. It then encounters beam splitter 13 which reflects approximately 50 percent of light beam 18 downward to lenses 19 which are conjugate to IRED 11 via beam splitter 13. The fundus area giving rise to reflected light beam 18 is thus imaged at the position of lenses 19. Lenses 19 then form images of the pupils of both eyes onto digital image sensor 20, because digital image sensor 20 is located conjugate to the pupils of both eyes via lenses 19. For illustration, the light from light beam 18 emerging from eye 10 is imaged by lenses 19 to form left pupil image 21 on digital image sensor 20. The right pupil image 22 is also imaged on digital image sensor 20 by lenses 19. Medium-bandwidth transmission optical filter 23 is placed between lenses 19, allowing most of the remaining near-infrared light originating from IRED 11 and contained within reflected light beam 18 to pass through to digital image sensor 20, while blocking essentially all light outside this band, especially the visible light reflected from the retinas and from the subject's eyes and face.

Digital image sensor 20 in FIG. 1 is typically a charge-coupled device (CCD) or a complementary metal-oxide-semiconductor (CMOS) device. The output (not shown) of digital image sensor 20 is connected to computing means, not shown, where conventional computerized image processing, well known in the art, is used to identify the X and Y positions of the centroids of the two pupil images 21 and 22, and, according to the present invention, the X and Y coordinates of the simultaneous images of the two pupils are recorded and are repetitively subtracted from one another over time, that is at time points 1, 2, 3, etc., by the computer, specifically $(X_R1-X_L1, Y_R1-Y_L1)$, $(X_R2-X_L2, Y_R2-Y_L2)$, $(X_R3-X_L3, Y_R3-Y_L3)$, etc., yielding "difference" X-Y values (Xdiff1, Ydiff1), (Xdiff2, Ydiff2), (Xdiff3, Ydiff3), etc., that are stored as a set in computer memory for a specified duration of viewing time, typically from 5 to 30 seconds. The "difference" X-Y values represent the relative positions of the two pupil images with respect to one another at time points 1, 2, 3, etc. The variability within the set of relative positions is calculated in real time, or subsequently, as a measure of the variability over time of the alignment between the two eyes. The greater the variability of the alignment between the two eyes over time, the greater the chance that a deficit of binocular function such as amblyopia or strabismus is present.

Note that the subject can and will look around at different portions of the video display. If binocular function is normal, the eyes will move together (conjugately) when scanning the display, meaning that they will move in the same direction and the same amount, locked together by the binocular vision mechanism. If this is the case, there will be little or no variability in the relative positions of the two pupils' images as detected by digital image sensor 20, and this minimum or absent variability will indicate normal binocular function. If, however, the movements of the two eyes are disconjugate, variability in the relative positions of the two pupils' images as detected by digital image sensor 20 will indicate a probable deficit of binocular function. In addition, if a deficit of binocular function is present, the normalized position of the pupil image of one eye may show more variability over time than the normalized position of the pupil image of the other eye, thus identifying the eye with the more variable normalized position to be the amblyopic or deviating eye.

In eye fixation studies, a common method of determining single eye fixation instability, when the data from an epoch of intended fixation comprise a set of recorded eye positions with X-Y coordinates, is the use of the bivariate contour ellipse [Timberlake G T, Sharma M K, Grose S A, Gobert D V, Gauch J M, Maino J H. Retinal location of the preferred retinal locus relative to the fovea in scanning laser ophthalmoscope images, *Optom. Vis. Sci.* 2005; 82:177-185]. In this method, on a plot of the set of X-Y eye positions, the minimum-area ellipse is calculated that contains a given percent of the plotted points, typically 68% of the points, representing +/−1 standard deviation of the eye positions surrounding the centroid. The larger the area of this ellipse (the "BCEA"), the greater the fixation instability. Likewise, if the area of the ellipse (the "BCEA") is small, the fixation is good.

According to embodiments of the present invention, the "difference" X-Y values, representing the relative positions of the two pupil images with respect to one another at time points 1, 2, 3, etc., comprise a two-dimensional collection of points for which a bivariate contour ellipse area (BCEA) may be calculated which contains a given percentage of the relative position points. If the BCEA is small, the conjugacy of the eye positions over time is good, but if the BCEA is larger than a threshold to be determined by experimentation, then a deficit of binocular function is likely present.

The BCEA method of determining variability in the relative positions of the two pupils' images with one another over time is only one such method of determining such variability. Other mathematical, graphical, or statistical methods may be used, with varied advantages. For example, there is evidence that amblyopic eyes exhibit more slow drifts when fixating than sound eyes [González E G, et al. *Invest Ophthalmol Vis Sci.* 2012; 53(9):5386-94]. Also, when strabismus is present (misalignment of the eyes—a defect of binocular vision), the amount of misalignment often varies in different directions of gaze, for example varying from looking at one portion of the video display to another portion. The centers of the bivariate contour ellipses containing "difference" X-Y values, calculated for successive short epochs of viewing, will therefore vary over time. Because such slow variation in conjugacy of the eye positions is also a valid indicator of deficits of binocular function, analyzing slow variation in conjugacy separately from more rapid variations in conjugacy can yield two metrics rather than simply one metric to identify deficits of binocular function.

Note that the stimulus provided to attract the subject's gaze need not be restricted to a movie on video display 17. The use of "difference" X-Y values as just described has the considerable advantage of allowing the use of an extended visible object without a specified fixation point, but other visible objects will also be suitable, for example a specified fixation point which is stationary or moving, or an extended scene containing a specified fixation point which is stationary or moving. A visible object seen by only one eye will suffice. In the extreme, even a sound in substantial darkness toward which the subject "looks" can be suitable.

If the subject's head rotates horizontally, tilts to either side, or moves forward or backward, the apparatus in FIG. 1 will detect apparent disconjugate movement of the two eyes from purely geometric considerations, even when no true disconjugate movement is present. Such false readings may be largely avoided by placing a small reflective adhesive dot on each lower lid, near the nose, and tracking the images of the two dots when also tracking the pupil images, using digital image sensor 20. Because pure eye movements do not substantially affect the relative positions of the reflective dots, but head movements do affect these relative positions, compensation for the head movement can be made via calculations to subtract out most of the head movement contributions to the apparent disconjugacy of the eye movements. [See: Irsch K, Ramey NA, Kurz A, Guyton D L, Ying H S. Video-based head movement compensation for novel haploscopic eye tracking apparatus. *Invest Ophthalmol Vis Sci.* 2009; 50:1152-1157.]

Figure 2:
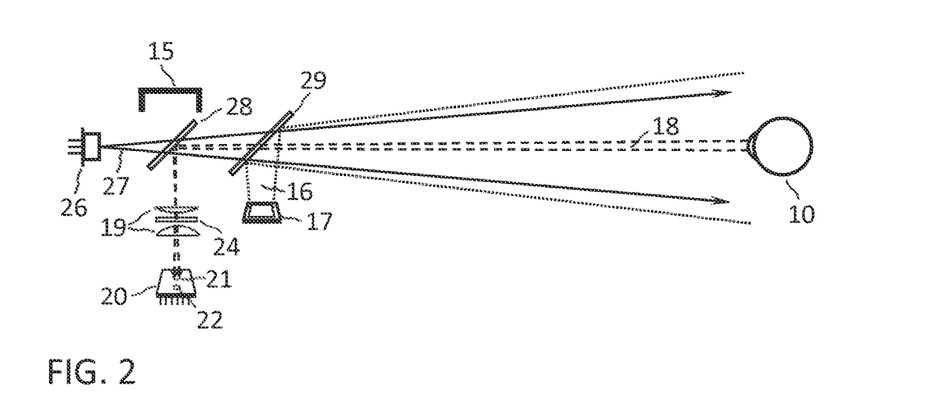
FIG. 2 illustrates a schematic diagram of an eye alignment monitor, using a near-infrared laser diode as the light source, and a digital image sensor according to another embodiment of the current invention.

FIG. 2 illustrates a schematic diagram of an eye alignment monitor identical in most respects to the eye alignment monitor illustrated in FIG. 1, with identical numbers identifying the same components. IRED 11 in FIG. 1 has been replaced in FIG. 2 by near-infrared laser diode 26, serving as an effective point source of near-infrared light. Other point light sources may be used, including a "point source" IRED, a near-infrared semi-luminescent diode, or a near-infrared gas or solid-state laser with a diverging lens. Medium-bandwidth optical filter 23 in FIG. 1 has been replaced by narrower-bandwidth filter 24 in FIG. 2, because the light from various effective point sources of light have narrower spectral bandwidths than the light from ordinary IRED's.

Laser diodes emit linearly polarized light, with the axis of polarization perpendicular to the major axis of the elliptically-shaped emitted beam. Near-infrared laser diode 26 in FIG. 2 is oriented with its major beam dimension horizontal, such that the elliptically-shaped near-infrared light beam 27 illuminates both pupils of the subject. The axis of polarization of near-infrared light beam 27 is thus vertical, as near-infrared light beam 27 passes through beam splitters 28 and 29 to illuminate both eyes of the subject.

Beam splitter 28 in FIG. 2 may be a non-polarizing beam splitter, preferably of the 50:50 type, in which case beam splitter 28 acts identically to beam splitter 13 in FIG. 1. But beam splitter 28 in FIG. 2 may alternatively be a polarizing beam splitter, in which case the vertically polarized near-infrared light beam 27 passes substantially unaltered through beam splitter 28, representing "p" polarization with respect to beam splitter 28. The advantage is that essentially no light is lost on the initial pass through beam splitter 28, and light trap 15 can easily absorb the minute amount of light that is reflected superiorly.

Beam splitter 29 in FIG. 2 may be an ordinary dichroic beam splitter identical to beam splitter 14 in FIG. 1, in which case it will act identically to beam splitter 14 in FIG. 1. But, alternatively, because beam splitter 29 in FIG. 2 is a tilted, thin-film optical element, it may be designed to have retardance equal to one quarter of the wavelength of the near-infrared light in light beam 27. If so, beam splitter 29, along with video display 17, may be rotated 45° (not shown) about the line connecting near-infrared laser diode 26 with the center point of the subject's eyes, converting the polarization state of near-infrared light beam 27 from linear polarization to circular polarization. Because much of the light reflected from the ocular fundus maintains circular polarization, but simply changes its handedness upon reflection, for example from right-handed circular polarization to left-handed, or left-handed to right-handed as the case may be, when reflected light beam 18 passes back through beam splitter 29, it is converted by the quarter-wave plate effect of beam splitter 29 into horizontally polarized light, representing "s" polarization with respect to beam splitter 28. This mostly horizontally ("s−") polarized light is largely reflected by polarizing beam splitter 28, thus without substantial loss of light from polarizing beam splitter 28. The advantage of the combination of polarizing beam splitter 28 and appropriately-oriented effective quarter-wave plate beam splitter 29 in FIG. 2 is that considerable light is conserved, because much less light is lost to polarizing beam splitter 28 in both the forward transmission direction and the backward reflection direction.

In the embodiments of the invention shown in both FIGS. 1 and 2, a small, bright reflected image of the light source from the front corneal surface will appear essentially in the same plane as each pupil image. This tiny, virtual image of the light source, is located only 1 mm posterior to each pupillary plane. The digital image sensors in the embodiments of the invention shown in FIGS. 1 and 2 can detect each of these small bright reflections, called "corneal light reflexes." Computerized image analysis that is similar to that used to locate the pupil images may be used to locate the positions of the corneal light reflexes. Via automated calculations, the position of each corneal light reflex with respect to the position of the pupil image of that eye may be used to calculate gaze direction, which calculation is relatively independent of head movement. Variations in the gaze directions of the two eyes over time may also be used to assess variability of the relative alignment of the two eyes with each other. A disadvantage of this method is that because the corneal light reflex and the pupil image move in the same direction with eye movement (the corneal light reflex moving about half as fast) the determination of changes in the distance between the corneal light reflex position and the pupil image position is only half as sensitive as the determination of changes in pupil image position itself.

Figure 3:
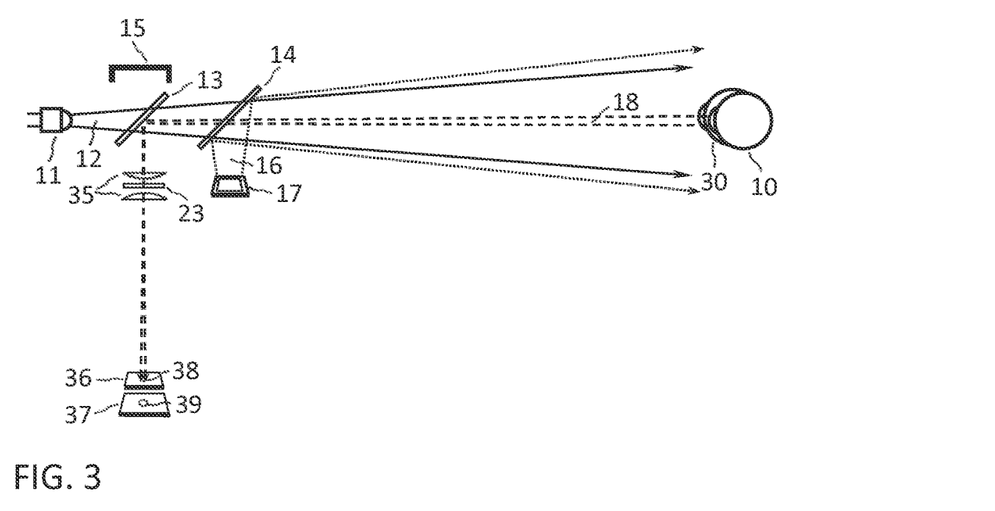
FIG. 3 illustrates a schematic diagram of an eye alignment monitor, using an IRED light source, and two X-Y position sensors, according to another embodiment of the current invention.

FIG. 3 illustrates a schematic diagram of another embodiment of an eye alignment monitor according to the present invention. The embodiment of the eye alignment monitor shown in FIG. 3 is identical in many respects to the eye alignment monitor shown in FIG. 1, with identical numbers identifying the same components. In addition to the subject's left eye 10 in FIG. 1, the subject's right eye 30 has been shown as well in FIG. 3, on the far side of left eye 10. Lenses 19 in FIG. 1 have been replaced by less powerful lenses 35 in FIG. 3. Digital image sensor 20 in FIG. 1 has been replaced by analog position sensors 36 and 37 in FIG. 3, receiving left pupil image 38 on position sensor 36, and right pupil image 39 on position sensor 37.

The use of analog position sensors 36 and 37 greatly simplifies the electronics required to identify the positions of pupil images 38 and 39. Each of continuous position sensors 36 and 37, with its associated analog electronics, produces voltages that are proportional to the X and Y coordinates of the intensity centroid of the spot of light (the respective pupil image) falling upon it, with extremely high precision (that is, to the nearest 1 to 2 microns with typical position sensors). Digital image sensors (CCD or CMOS image sensors) are available with such precision, but those that are large enough to provide such high precision over the typical 10×10 mm sensor surface of typical analog position sensors are prohibitively expensive, slow, and electronically complicated.

Each of the analog position sensors 38 and 39 also produces sum voltages that are proportional to the total intensity of the light detected in the X channel and in the Y channel. These voltages may be used to normalize the X and Y position signals respectively, by dividing the X and Y position signals by the X and Y sum signals respectively, so that the resulting normalized X and Y position signals are relatively independent of total light intensity. Also, because the processed sum signals are proportional to the total intensity of the detected light, these sum signals may be used to adjust automatically the intensity of IRED 11, within safe limits, for optimum detection by analog position sensors 38 and 39 of the light in the pupil images while not detecting lower-level reflected near-infrared light from the sclera and skin.

The outputs (not shown) of position sensors 36 and 37 are connected via an analog-to-digital converter to computing means (not shown), whereby the X and Y coordinates of both pupil images are repetitively digitized and stored. As discussed relative to the apparatus of FIG. 1, the stored X and Y coordinates of the simultaneous images of the two pupils are repetitively subtracted from one another over time, that is at time points 1, 2, 3, etc., by the computer, specifically $(X_R1-X_L1, Y_R1-Y_L1)$, $(X_R2-X_L2, Y_R2-Y_L2)$, $(X_R3-X_L3, Y_R3-Y_L3)$, etc., yielding "difference" X-Y values (Xdiff1, Ydiff1), (Xdiff2, Ydiff2), (Xdiff3, Ydiff3), etc., that are stored as a set in computer memory for a specified duration of viewing time, typically from 5 to 30 seconds. The "difference" X-Y values represent the relative positions of the two pupil images with respect to one another at time points 1, 2, 3, etc. The variability within this set of relative positions is then calculated as a measure of the variability over time of the alignment between the two eyes, as discussed relative to the apparatus of FIG. 1. The greater the variability of the alignment between the two eyes over time, the greater the chance that a deficit of binocular function such as amblyopia or strabismus is present.

A primary advantage of the eye alignment monitor of the current invention is its ability to assess the variability of the relative alignment of the two eyes with each other without requiring fixation of either eye on a specific point. Note that the subject can and will look around at different portions of the movie on the video display. If binocular function is normal, the eyes will move together (conjugately) when scanning the display, meaning that they will move in the same direction and the same amount, maintaining the same alignment with one another because of the "tone" established by the binocular vision mechanism—with conjugate movement occurring even when one eye is covered or when both eyes are blurred (for example without corrective glasses in place). If the eyes move about conjugately, there will be little or no variability in the relative positions of the two pupils' images as detected by analog position sensors 36 and 37, and this minimum or absent variability will indicate normal binocular function. If, however, the movements of the two eyes are not conjugate, variability in the relative positions of the two pupils' images as detected by analog position sensors 36 and 37 will indicate a probable deficit of binocular function. In addition, if a deficit of binocular function is present, the normalized position of the pupil image of one eye will show more variability over time than the normalized position of the pupil image of the other eye, thus identifying the eye with the more variable normalized position to be the amblyopic or strabismic eye.

Figure 4:
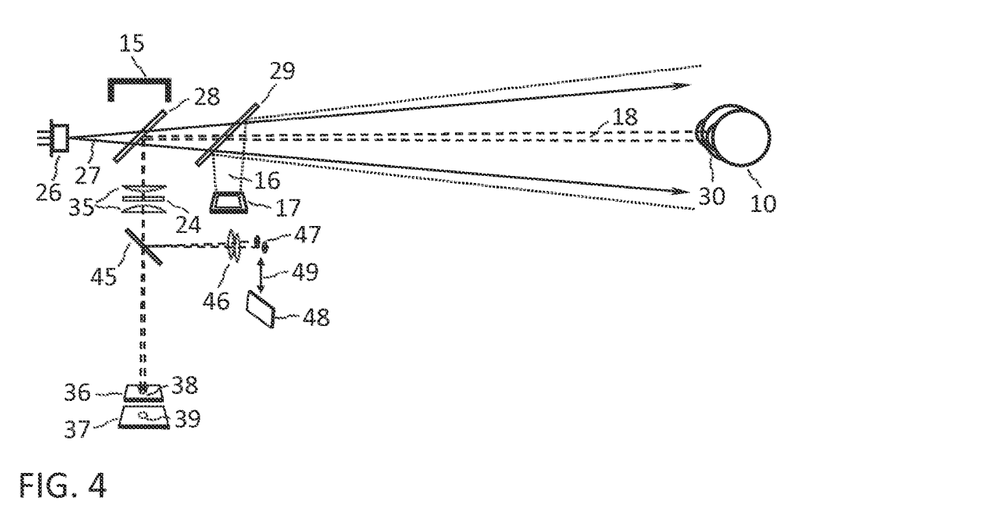
FIG. 4 illustrates a schematic diagram of an eye alignment monitor, using a near-infrared laser diode as the light source, and two X-Y position sensors, according to another embodiment of the current invention.

FIG. 4 illustrates a schematic diagram of an eye alignment monitor that is identical in many respects to the eye alignment monitors shown in FIGS. 2 and 3, with identical numbers identifying the same components. Specifically, the eye alignment monitor shown in FIG. 4 has the same near-infrared laser diode 26, near-infrared light beam 27, and beam splitters 28 and 29 as in FIG. 2. In addition, the eye alignment monitor shown in FIG. 4 has the same right eye 30 shown, lenses 35, and the analog position sensors 36 and 37 as in FIG. 3. Thus the eye alignment monitor shown in FIG. 4 is a hybrid of the two eye alignment monitors shown in FIG. 2 and FIG. 3.

In addition, FIG. 4 shows added beam splitter 45 between lenses 35 and analog position sensors 36 and 37. A portion of returning light beam 18 from the pupil of left eye 10, on its way to analog position sensor 36, is thus deflected by beam splitter 45 and is focused by one of the lenses 46 onto one of two bull's-eye photodetectors 47. Lenses 35 are conjugate to the point light source of near-infrared laser diode 26, and it is the aperture occupied by lenses 35 that is focused by lenses 46 onto the bull's-eye photodetectors 47. The two eyes' double-pass images of the point source of light from near-infrared laser diode 26 appear superimposed (but coming from different angles) in the aperture occupied by lenses 35, and these images are focused by lenses 46 onto bull's-eye photodetectors 47, one for the right eye and one for the left eye of the subject. If each eye of the subject is focused properly on video display 17, then the double-pass images of the point source of light from near-infrared laser diode 26 will be small images, mostly falling upon the center active areas of the bull's-eye photodetector 47. If, however, either eye of the subject is not focused properly on video display 17, then its double pass image of the point source of light from near-infrared laser diode 26 will be blurred, with a portion of the blurred light falling on the annular active area of its bull's-eye photodetector 47. The signal from the annular active area is subtracted from, or divided into, the signal from the center active area in a normalized manner. A high signal level signifies good focus of the double pass image; a low signal level signifies significant refractive error, or defocus for other reasons, of that eye of the subject. The use of bull's eye photodetectors for this purpose is well known in the art [U.S. Pat. No. 6,027,216 and Hunter D G, Nusz K J, Gandhi N K, Quraishi I H, Gramatikov B I, Guyton D L. Automated detection of ocular focus. *J Biomed Optics* 2004; 9:1103-9].

In FIG. 4, the bull's-eye photodetectors 47 may be replaced by digital image sensor 48, as illustrated by double-ended arrow 49. The two double-pass images of near-infrared laser diode 26 will thus be formed on digital image sensor 48, and, with appropriate conventional image processing, the quality of focus of those two double pass images can be assessed to determine the focus or defocus state of the two eyes 10 and 30 of the subject.

Figure 5:
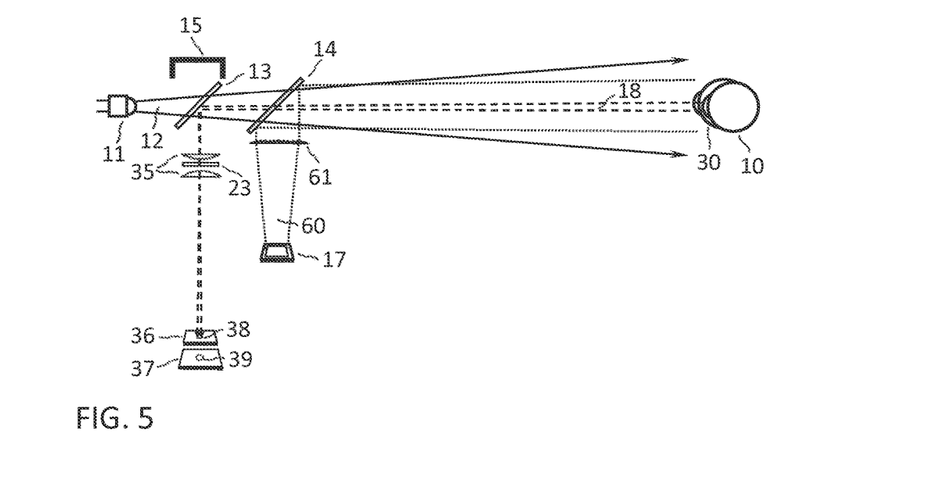
FIG. 5 illustrates a schematic diagram of an eye alignment monitor, using an IRED light source and two X-Y position sensors, along with the object viewed by the subject being imaged at a far distance or at infinity, according to another embodiment of the current invention.

FIG. 5 illustrates a schematic diagram of an eye alignment monitor identical in most respects to the eye alignment monitor illustrated in FIG. 3, with identical numbers identifying the same components. In FIG. 5, however, visible light beam 60 from video display 17 is substantially collimated by converging Fresnel lens 61 such that the movie displayed on video display 17 appears at a far distance or at infinity to the subject. This is done for the purpose of avoiding convergence of the eyes by the subject onto a near object, not only to avoid the undesirable effect of convergence in damping small eye movements, but also to avoid varying convergence which can interfere with the determination of variability of the relative alignment of the two eyes with each other. Converging Fresnel lens 61 could alternatively be an ordinary converging glass lens, but because both eyes must view the video display imaged in the distance, a relatively large diameter glass lens would be necessary, at least 75 mm in diameter, to extend beyond the interpupillary distance of the subject, producing greater weight and more aberration, with particularly more distortion, than converging Fresnel lens 61.

Figure 6:
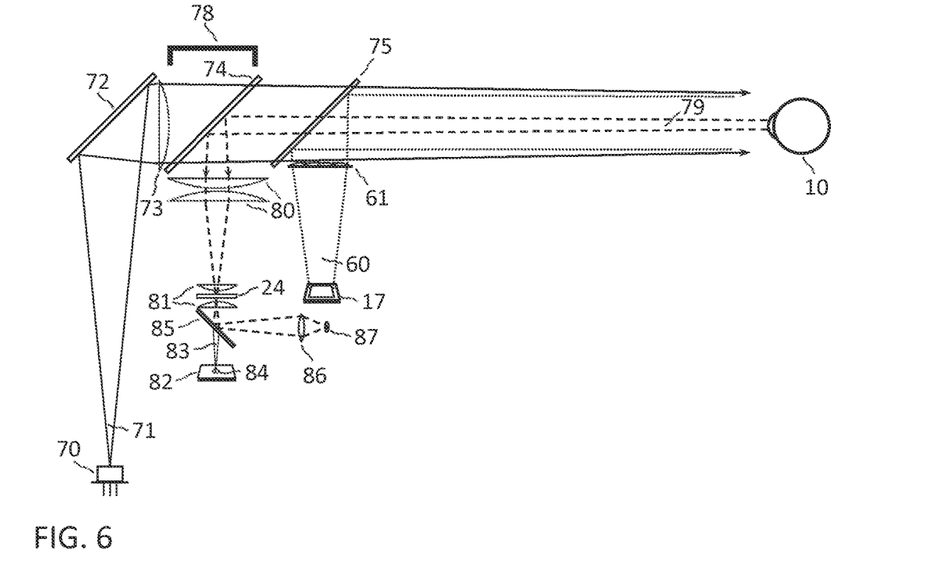
FIG. 6 illustrates a schematic diagram of an eye alignment monitor, using a near infrared laser diode as the light source, two X-Y position sensors, and the object viewed by the subject imaged at a far distance or at infinity, and the near-infrared laser diode light source also imaged as if coming from a far distance or at infinity, optically conjugate with the visible object viewed by the subject, according to another embodiment of the current invention.

FIG. 6 illustrates a schematic diagram of an eye alignment monitor that is similar to the eye alignment monitor shown in FIG. 5, with identical numbers identifying the same components. In FIG. 6, however, a point light source is used, in this case near-infrared laser diode 70, which is imaged to be optically conjugate with the movie on video display 17, taking into account the chromatic aberration of the subject's eyes. Specifically, the near-infrared laser diode 70 emits beam of light 71 that is reflected by mirror 72, is converged by lens 73, and passes through beam splitters 74 and 75 to illuminate left eye 10 of the subject. Visible light beam 60 from the movie on video display 17 is collimated by converging Fresnel lens 61 and is then reflected by beam splitter 75 toward left eye 10 of the subject. Because of the substantial collimation of visible light beam 60 by converging Fresnel lens 61, eye 10 of the subject sees the movie from video display 17 as if it is at a far distance, or at infinity. As in FIG. 5, this is done for the purpose of avoiding convergence of the eyes by the subject onto a near object, not only to avoid the undesirable effect of convergence in damping small eye movements, but also to avoid varying convergence which can interfere with the determination of variability of the relative alignment of the two eyes with each other. The additional goal in FIG. 6 is to have the point light source from near-infrared laser diode 70 focused in substantially the same plane in the back of left eye 10 as the plane where visible light beam 60 from the movie on video display 17 comes to focus. But because of the chromatic aberration of the human eye, the near-infrared light beam 71 must be converged by lens 73 to have approximately 0.75 to 1.00 diopter of convergence as it enters the pupil of eye 10 in order to come to focus in the same plane in the back of the eye as collimated visible light beam 60 from the movie on video display 17.

Beam splitter 74 may be a 50:50 beam splitter, as was the case with beam splitter 13 in FIGS. 1 and 3. Light trap 78 is provided in FIG. 6 to absorb the superiorly reflected light from beam splitter 74, preventing that light from returning back through beam splitter 74 to the detection system below. Alternatively, beam splitter 74 may be a polarizing beam splitter, similar to beam splitter 28 in FIGS. 2 and 4, as long as quarter-wave retardance at 45° is provided between beam splitter 74 and left eye 10, as described for FIG. 2. This quarter-wave retardance may be designed into beam splitter 75 in FIG. 6, provided that beam splitter 75, converging Fresnel lens 61, and video display 17 are all rotated as a unit 45° about the horizontal optical axis of the eye alignment monitor (this rotation is not shown). Alternatively, the quarter wave retardance may be supplied by an added double-pass quarter wave retarder with fast axis at 45° (not shown), with this retarder tilted appropriately to avoid back reflections to the detection system.

To maximize light preservation, beam splitter 75 is preferably designed as a dichroic beam splitter, with substantially 100 percent transmittance of the near-infrared light beam 71 and having high reflectance for visible light beam 60. As noted just above, if beam splitter 74 is a polarizing beam splitter, then beam splitter 75 can also be designed to have quarter-wave retardance for the near-infrared light in light beam 71, to substantial advantage in conserving this near-infrared light, as previously explained for FIG. 2.

That portion of near-infrared light beam 71 that enters the pupil of eye 10 is partially reflected by the rear inside surfaces (fundus) of the eye, and a portion of this reflected light (about 1/1000 of the original light beam entering the eye) emerges from the pupil of eye 10, constituting reflected light beam 79, travelling back toward the original light source, that is toward near-infrared laser diode 70. Reflected light beam 79 passes through beam splitter 75. It then encounters beam splitter 74 which reflects a portion of light beam 79 downward to lenses 80 which are substantially conjugate to lens 73 via beam splitter 74. Lenses 80 act upon reflected light beam 79 (the light reflected from the retina) to form the double-pass image of the point light source of near-infrared laser diode 70 in the plane of lenses 81. Lenses 81 are conjugate via lenses 80, beam splitter 74, lens 73, and mirror 72 to the point light source of near-infrared laser diode 70.

Lenses 81, in the plane of the double-pass image of the point light source from near infrared laser diode 70, serve to form, onto position sensor 82, via light beam 83 (originating from the plane of the pupil of left eye 10, not traced), pupil image 84 from the subject's left eye 10. Movement of eye 10 will thus be measured as a change in position of pupil image 84 on position sensor 82.

Beam splitter 85, placed in the path of the rays of light between lenses 81 and position sensor 82, serves to direct a portion of those rays to lens 86. Lens 86 re-images, from the plane of lenses 81, onto bull's-eye photodetector 87, the double-pass image of the original point light source from near-infrared laser diode 70, as carried by reflected light beam 79 returning from the fundus of left eye 10. Thus the goodness of focus of left eye 10 of the subject, on the visible light movie on video display 17, can be judged by the focus, on bull's-eye photodetector 87, of the double pass image of the near-infrared light from the point light source of near-infrared laser diode 70, as explained in detail earlier for FIG. 4.

The embodiment of the eye alignment monitor shown in FIG. 6 is only illustrated for left eye 10 of the subject. Making the optics of this arrangement wide enough for binocular viewing in the distance requires more elements. Converging Fresnel lens 61 and beam splitter 75 may be made wide enough to accommodate viewing by both eyes of video display 17 imaged in the distance, and beam splitter 74, light trap 78, and mirror 72 may be made wide enough, but the remaining optics must be duplicated for the other eye (not shown), including providing a second near-infrared laser diode, a second set of all other lenses, a second position sensor, and a second bull's-eye photodetector. An advantage of having essentially separate and substantially parallel detection channels for the two eyes of the subject is that to and fro movements of the subject's head, or of the hand-held apparatus, will interfere less with the measure of conjugacy of the positions of the images of the two pupils.

Figure 7:
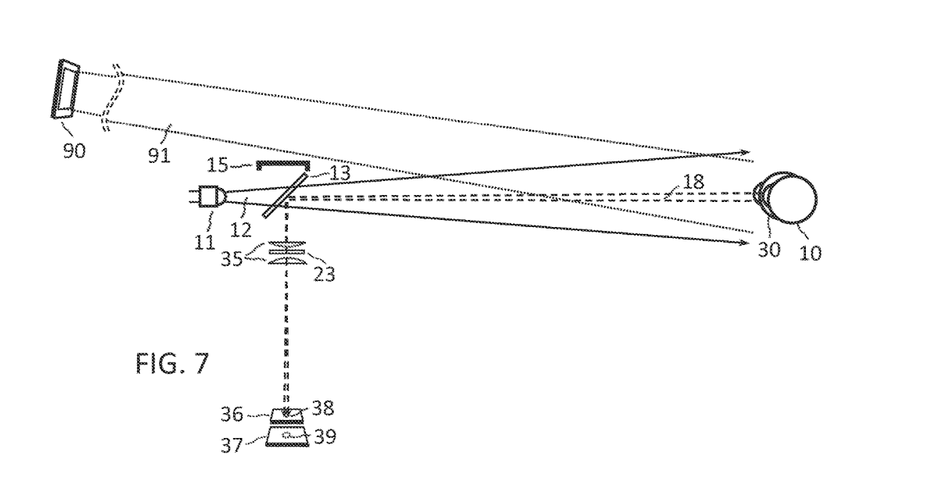
FIG. 7 illustrates a schematic diagram of an eye alignment monitor, using an IRED light source and two X-Y position sensors, along with the object viewed by the subject being physically placed at a relatively far distance, according to a preferred embodiment of the current invention.

FIG. 7 illustrates a schematic diagram of a preferred embodiment of an eye alignment monitor according to the present invention. It is identical in most respects to the eye alignment monitor illustrated in FIG. 5, with identical numbers identifying the same components. From FIG. 5, however, image display 17, converging Fresnel lens 61, and dichroic beam splitter 14 have all been removed from the apparatus, to be replaced in FIG. 7 by conventional external image display 90, located at a greater distance from the subject than the remaining apparatus, to minimize convergence, and viewed over the top of the apparatus by eyes 10 and 30. Conventional external image display 90 may most conveniently be a small television or computer monitor. Light beam 91 from image display 90 in the distance passes over the apparatus to eyes 10 and 30. In addition to advantages shared with the eye alignment monitor depicted in FIG. 5, the eye alignment monitor depicted in FIG. 7 is simplified and less complex, without having to have the video display incorporated within it.

Figure 8:
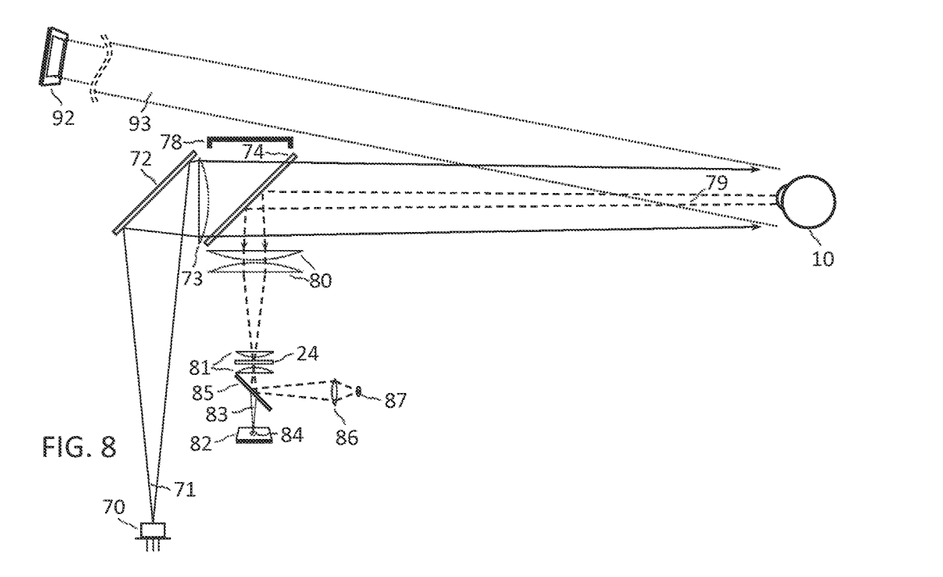
FIG. 8 illustrates a schematic diagram of an eye alignment monitor, using a near infrared laser diode as the light source and two X-Y position sensors, along with the object viewed by the subject being physically placed at a relatively far distance, and the near-infrared laser diode light source also imaged as if coming from a far distance or at infinity, optically conjugate with the visible object viewed by the subject, according to another embodiment of the current invention.

FIG. 8 illustrates a schematic diagram of an eye alignment monitor that is identical in most respects to the eye alignment monitor illustrated in FIG. 6, with identical numbers identifying the same components. From FIG. 6, however, image display 17, converging Fresnel lens 61, and dichroic beam splitter 75 have all been removed from the apparatus, to be replaced in FIG. 8 by conventional external image display 92, located at a distance from the subject to minimize convergence, and viewed over the top of the apparatus by eyes 10 and 30. Conventional external image display 92 may most conveniently be a small television or computer monitor. Light beam 93 from image display 92 in the distance passes over the apparatus to eyes 10 and 30. In addition to advantages shared with the eye alignment monitor depicted in FIG. 6, the eye alignment monitor depicted in FIG. 8 is simplified and less complex, without having to have the video display incorporated within it.

The embodiment of the eye alignment monitor shown in FIG. 8 is only illustrated for left eye 10 of the subject. To avoid unwanted optical aberrations, and to make the optics of this arrangement wide enough for binocular viewing in the distance, more optical elements are required. Converging Fresnel lens 61, beam splitters 74 and 75, light trap 78, and mirror 72 may be made wide enough, but the remaining optics must be duplicated for the other eye (not shown), including providing a second near-infrared laser diode, a second set of all other lenses, a second position sensor, and a second bull's-eye photodetector.

The optical axes of the eye alignment detection system in FIG. 7, and of the eye alignment detection system and focus detection system in FIG. 8, are not coaxial with the patient's lines of sight. This makes little difference, however, because the subject's eyes will still retro-reflect the light from light source 11 in FIG. 7, or from light source 70 in FIG. 8, back toward that respective source by the principle of conjugacy, resulting in bright pupil images. The subject's pupils will be viewed from 5° to 10° below the lines of sight, but good pupil images will still be seen from this relatively small offset angle, and the relative positions of the pupil images that are formed on the analog position sensors will still be obtained and calculated in the same way. Likewise, the refractive error of the human eye is relatively constant within 10° of the line of sight, so the assessment of focus by the focus detection system in FIG. 8 will be perfectly adequate for screening purposes.

Figure 9:
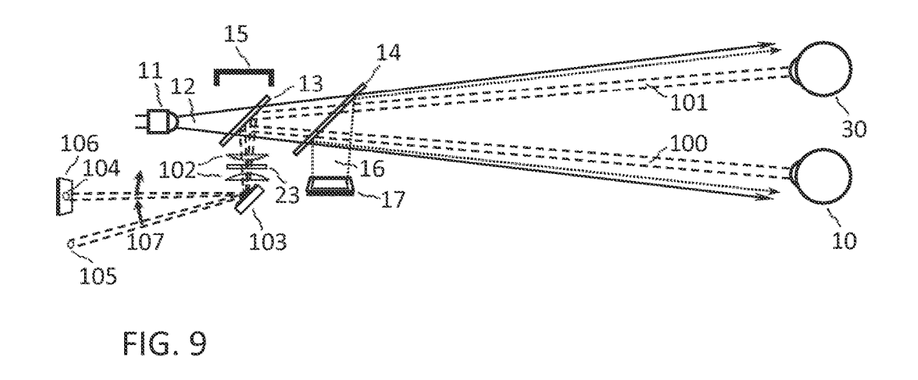
FIG. 9 illustrates a schematic diagram of an eye alignment monitor, using an IRED light source, one X-Y position sensor, and a digital micro-mirror device (DMD), according to another embodiment of the current invention.

FIG. 9 illustrates a schematic diagram of an eye alignment monitor similar in many respects to the eye alignment monitor illustrated in FIG. 3, with identical numbers identifying the same components. FIG. 9, however, is viewed from the top of the apparatus, such that the subject's eyes 10 and 30 are illustrated side-by-side rather that one behind the other. Light emerges from the pupils of eyes 10 and 30, constituting light beams 100 and 101 respectively, reflected from the retinas of eyes 10 and 30, traveling back toward IRED 11, the original source. Reflected light beams 100 and 101 pass through beam splitter 14. They then encounter beam splitter 13 which reflects approximately 50 percent of each of light beams 100 and 101 downward through lenses 102 and medium-bandwidth optical filter 23 to digital micro-mirror device 103 which is conjugate to IRED 11 via lenses 102 and beam splitter 13. The fundus areas giving rise to reflected light beams 100 and 101 are thus imaged substantially in superimposition at the position of digital micro-mirror device 103. Lenses 102 form images 104 and 105 of the pupils of eyes 10 and 30 respectively in the plane of analog position sensor 106, because the plane of analog position sensor 106 is located conjugate to the plane of the pupils of both eyes via lenses 102. Lenses 102, along with medium-bandwidth optical filter 23, may be placed between beam splitter 13 and digital micro-mirror device 103 as shown in FIG. 9, or they may be placed just to the left of digital micro-mirror device 103. Digital micro-mirror device 103 has two alternative states that are switched rapidly back and forth electronically. In the illustrated state, digital micro-mirror device 103 reflects light beam 100 onto analog position sensor 106, forming image 104 of the pupil of eye 10 on analog position sensor 106. In the alternative state, the micro-mirrors on digital micro-mirror device 103 all tilt in unison, deflecting the light beams forming pupil images 104 and 105 approximately 25°, as illustrated by arrows 107, such that pupil image 105 will then be formed on analog position sensor 106. During the momentary alternating times that pupil images 104 and 105 fall on analog position sensor 106, their positions are sensed as described for the apparatus of FIG. 3. Thus the apparatus in FIG. 9 obtains the relative positions of the two pupil images in a rapidly alternating manner via alternating reflections of the two pupil images by the digital micro-mirror device 103 onto a single analog position sensor. The advantage is that only one analog position sensor is needed.

It should be noted that the device and method of the present invention can be executed using a computing device such as a microprocessor, hard drive, solid state drive or any other suitable computing device known to or conceivable by one of skill in the art. The computing device can be programmed with a non-transitory computer readable medium that is programmed with steps to execute the different stimulation levels, patterns, and configurations available.

Any such computer application will be fixed on a non-transitory computer readable medium. It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media include, but are not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device.

Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An eye alignment monitor to detect variability of the relative alignment of the two eyes of a subject with each other, comprising:
   a stimulus to attract the gaze of said subject;
   at least one light source for illumination of both eyes of the subject;
   means for tracking the positions of both eyes simultaneously; and
   means for repetitive calculation of the relative positions of said both eyes with respect to each other,
   whereby analysis of changes in the relative positions of said both eyes with respect to each another over time yields a measure of the variability of the relative alignment of the two eyes with each other, for the purpose of detecting deficits of binocular function.

2. An eye alignment monitor according to claim 1, wherein said means for tracking the positions of both eyes simultaneously comprises means for tracking the positions of the images of the pupils of both eyes simultaneously.

3. An eye alignment monitor according to claim 2, wherein said means for tracking the positions of images of the pupils of both eyes simultaneously comprises at least one digital image sensor, with said two pupil images falling upon said at least one digital image sensor.

4. An eye alignment monitor according to claim 3, wherein the position of the corneal light reflections of said light source from each of said eyes is also detected by said digital image sensor, enabling not only pupil tracking but also tracking of gaze direction by means of the relative position of said corneal light reflection with respect to the pupil position of each of said eyes.

5. An eye alignment monitor according to claim 2, wherein said means for pupil tracking comprises an X-Y position sensor for each of said pupil images that is tracked, upon which said pupil image is formed.

6. An eye alignment monitor according to claim 2, wherein said means for pupil tracking comprises a single X-Y position sensor upon which the images of said both pupils are alternately directed by optical means and are thereby tracked in rapid alternation.

7. An eye alignment monitor according to claim 6, wherein said optical means comprises a digital micro-mirror device.

8. An eye alignment monitor according to claim 1, wherein said means for tracking the positions of both eyes simultaneously comprises means for tracking one of: the positions of the corneal light reflections from both eyes simultaneously, the positions of the corneal/scleral junctions of both eyes simultaneously, the projections of fundus landmarks of both eyes simultaneously using retinal birefringence scanning, the positions of anatomic features of both eyes simultaneously using optical coherence tomography, and the positions of both eyes simultaneously using scleral search coil recordings.

9. An eye alignment monitor according to claim 1, wherein said stimulus comprises one of: a stationary small fixation point, a moving small fixation point, an extended object containing a specified stationary fixation point, an extended object containing a specified moving fixation point, an extended object such as a movie on a video display without a specified fixation point, a visible object seen by both eyes, a visible object seen by only one eye, and a sound which attracts the gaze of the subject.

10. An eye alignment monitor according to claim 9, wherein said at least one light source comprises a substantially point source of light and is further positioned at an optical distance from the eyes of the subject so as to be conjugate with said visible object, taking into account the chromatic aberration of said subject's eyes between visible light and the wavelength of said light source, such that if the subject is focused with both eyes on said visible object, the light from said point source of light will be focused on each of the subject's retinas and will be retro-reflected from the fundus of each eye to come to focus in at least one external image plane that is conjugate to said point source of light, whereby analysis of the spatial distribution of the light in said at least one external image plane yields an assessment of how well the corresponding subject's eye is focused on said visible object, for the purpose of detecting defocus of said subject's eye.

11. An eye alignment monitor according to claim 10, wherein said at least one external image plane that is conjugate to said at least one light source contains a digital image sensor that is used to analyze the spatial distribution of the light in said external image plane, for the purpose of detecting defocus of said subject's eye.

12. An eye alignment monitor according to claim 10, wherein said at least one external plane that is conjugate to said at least one light source contains a bull's-eye photodetector that receives the double-pass image of said light source from one of said eyes, whereby the goodness of focus of said double-pass image is analyzed by comparing the signal from the annulus of said bull's-eye photodetector with the signal from the center area of said bull's-eye photodetector.

13. An eye alignment monitor according to claim 1, where said at least one light source is positioned substantially coaxial with the optics of said tracking means, such that bright pupils are seen and tracked by said tracking means.

14. An eye alignment monitor according to claim 13, wherein said at least one light source comprises at least one of: a light-emitting diode, a near-infrared light-emitting diode, a point source light-emitting diode, a semi-luminescent diode, a near-infrared semi-luminescent diode, a laser diode, a near-infrared laser diode, a gas laser diverged with a lens, and a solid-state laser diverged by a lens.

15. An eye alignment monitor according to claim 1, wherein said gaze-attracting stimulus is localized by said subject at a distance beyond the eye alignment monitor, such that the subject gazes toward said stimulus with less convergence of the eyes, thus decreasing the tendency for variable convergence to interfere with measurement of the variability of the relative alignment of the two eyes with each other when gazing toward said stimulus.

16. An eye alignment monitor according to claim 15, wherein said gaze-attracting stimulus comprises a virtual image of a visible object and said light source comprises at least one substantially point source of light that is imaged so as to be conjugate with said virtual image at a distance beyond the apparatus, taking into account the chromatic aberration of said subject's eyes between visible light and the wavelength of said light source, such that if the subject is focused with both eyes on said visible object, the light from said at least one point source of light will be focused on each of the subject's retinas and will be retro-reflected from the fundus of the corresponding eye to come to focus in at least one external image plane that is conjugate to said point source of light, whereby analysis of the spatial distribution of the light in said external image plane yields an assessment of how well said subject's eye is focused on said visible object, for the purpose of detecting defocus of said eye.

17. An eye alignment monitor according to claim 1, wherein said gaze-attracting stimulus is physically placed at a distance, farther than the eye alignment monitor, such that the subject views said stimulus with less convergence of the eyes, thus decreasing the tendency for variable convergence to interfere with measurement of the variability of the relative alignment of the two eyes with each other when gazing toward said stimulus.

18. An eye alignment monitor according to claim 17, wherein said gaze-attracting stimulus comprises a visible object and light source comprises at least one substantially point source of light that is imaged so as to be conjugate with said visible object, with said visible object physically placed at a distance farther than the remaining apparatus, taking into account the chromatic aberration of said subject's eyes between visible light and the wavelength of said light source, such that if the subject is focused with both eyes on said visible object, the light from said at least one point source of light will be focused on each of the subject's retinas and will be retro-reflected from the fundus of the corresponding eye to come to focus in at least one external image plane that is conjugate to said point source of light, whereby analysis of the spatial distribution of the light in said external image plane yields an assessment of how well said subject's eye is focused on said visible object, for the purpose of detecting defocus of said eye.

19. A method to detect variability of the relative alignment of the two eyes of a subject with each other, comprising:
  attracting the gaze of said subject with a stimulus;
  illuminating both eyes of the subject by at least one light source generating reflected light beams from a left pupil and a right pupil of the subject;
  reflecting the generated reflected light beams onto a pair of lenses;
  forming images of the pupils of both eyes onto a digital image sensor with the lenses;
  tracking the positions of both eyes simultaneously with the digital image sensor, which generates an output of the positions of both eyes;
  calculating repetitively the relative positions of said both eyes with respect to each other from the output of the digital image sensor using a computing device; and
  analyzing changes in the relative positions of said both eyes with respect each another over time to yield a measure of the variability of the relative alignment of the two eyes with each other, for the purpose of detecting deficits of binocular function.

20. A method according to claim 19 where said stimulus comprises a visible object, said means for tracking the positions of both eyes simultaneously comprise means for tracking the positions of images of the pupils of both eyes simultaneously, and the relative positions of said both eyes are defined by the relative positions of the images of the pupils of said both eyes.

* * * * *